United States Patent
D'Agostino

(10) Patent No.: US 8,225,673 B2
(45) Date of Patent: Jul. 24, 2012

(54) METHOD OF MANUFACTURING AND TESTING MONOFILAMENT AND MULTI-FILAMENTS SELF-RETAINING SUTURES

(75) Inventor: William L. D'Agostino, Hamden, CT (US)

(73) Assignee: Ethicon, Inc., Somerville, NJ (US)

( * ) Notice: Subject to any disclaimer, the term of this patent is extended or adjusted under 35 U.S.C. 154(b) by 936 days.

(21) Appl. No.: 12/262,953

(22) Filed: Oct. 31, 2008

(65) Prior Publication Data

US 2009/0107965 A1 Apr. 30, 2009

Related U.S. Application Data

(60) Provisional application No. 60/984,331, filed on Oct. 31, 2007.

(51) Int. Cl.
*G01N 3/08* (2006.01)

(52) U.S. Cl. .................. 73/826; 73/760; 73/830

(58) Field of Classification Search .............. 73/760, 73/826, 830
See application file for complete search history.

(56) References Cited

U.S. PATENT DOCUMENTS

| | | | |
|---|---|---|---|
| 4,300,397 A * | 11/1981 | Brest van Kempen | 73/818 |
| 5,500,991 A * | 3/1996 | Demarest et al. | 29/407.08 |
| 6,727,716 B1 * | 4/2004 | Sharif | 324/756.03 |
| 6,906,341 B2 * | 6/2005 | Byun et al. | 257/48 |
| 7,212,019 B2 * | 5/2007 | Schneegans et al. | 324/755.11 |
| 7,343,791 B2 * | 3/2008 | Cuevas et al. | 73/160 |
| 2011/0046669 A1 * | 2/2011 | Goraltchouk et al. | 606/228 |

* cited by examiner

Primary Examiner — Max Noori

(57) ABSTRACT

The present invention relates to self-retaining ("barbed") systems for surgical procedures, methods of manufacturing self-retaining systems for surgical procedures, included their uses and testing. In various embodiments of the invention, a device and method for barbing sutures uses a laser to cut the suture under appropriate temperature and tensile strength conditions. In various embodiments of the invention, a device and method tests the tensile strength and elasticity of a barbed monofilament or multifilament suture. In various embodiments of the invention, a potting material can be used to retain one end of the suture for manufacture or testing.

20 Claims, 2 Drawing Sheets

METHOD OF MANUFACTURING AND TESTING MONOFILAMENT AND MULTI-FILAMENTS SELF-RETAINING SUTURES

FIELD OF THE INVENTION

The present invention relates to self-retaining ("barbed") systems for surgical and cosmetic procedures, methods of manufacturing self-retaining systems for surgical and cosmetic procedures, including combining synthetic, natural and recombinant polymer materials, coatings for modifying the suture properties and methods of testing self-retaining sutures. A device and method improves the testing and cutting of self-retaining monofilament or multifilament sutures.

BACKGROUND OF THE INVENTION

Sutures are stitches that surgeons use to hold skin, internal organs, blood vessels and other tissues of the human body together, after such tissues have been severed by injury or surgery. Depending on the application, sutures must be flexible, sufficiently strong to not break, non-toxic and non-hypoallergenic, in order to avoid adverse reactions in the patient's body. The flexibility of the suture is important in situations where the sutures must be drawn and knotted easily. In addition, the suture must lack the so called "wick effect", which means that sutures must not allow fluids to penetrate the body or organ from the outside.

Suture materials can be broadly classified as being bioabsorbable and non-bioabsorbable materials. Bioabsorbable sutures will break down harmlessly in the body over time without intervention. Non-bioabsorbable sutures must either be left indefinitely in place or manually removed. The type of suture used varies depending on the operation, with a major criteria being the demands of the location of the wound or incision and the local environment. For example, sutures to be placed internally would require re-opening of the patient's body if the suture were to be removed. Alternatively, sutures which address a wound or incision on the exterior of the patient's body can be removed within minutes, and without re-opening the wound. As a result, bioabsorbable sutures are often used internally and non-bioabsorbable sutures externally. Further, sutures to be placed in a stressful environment, for example near the heart where there is constant pressure and movement or near or on the bladder, may require specialized or stronger materials to perform the desired role. Usually such sutures can be either specially treated, or made of special materials, and are often non-bioabsorbable to reduce the risk of degradation Suture sizes are defined by the United States Pharmacopeia (U.S.P.) the official public standards-setting authority for all prescription and over-the-counter medicines, dietary supplements, and other healthcare products manufactured and sold in the United States. Sutures can be manufactured ranging in decreasing sizes from #6 to #11/0, where #5 corresponds with a heavy braided suture for orthopedics, while #10/0 is a fine monofilament suture for ophthalmic applications. The actual diameter of thread for a given U.S.P. size differs depending on the suture material class.

A suture containing 'tissue retainers' or 'barbs' can be useful as a wound closure device. Such self-retaining (barbed) suture systems have previously been developed for a variety of surgical procedures. The self-retaining suture includes an elongated body and a plurality of tissue retainers projecting from the body. Each tissue retainer helps the suture resist movement in a direction opposite from which the tissue retainer faces. The disposition of the tissue retainers on the suture body can be ordered, e.g., staggered, spiral, overlapping, or random. Also, the tissue retainers can be configured with a specific angle, depth, length and separation distance.

SUMMARY OF THE INVENTION

In an embodiment of the invention, sutures include tissue retainers and self-retaining sutures can be tested for tensile strength (including extension-to-break strength) by affixing one end of the suture in a container and retaining the suture in the container by adding a potting mixture. In an embodiment of the invention, the potting mixture is light sensitive and changes from a liquid to a solid upon exposure to appropriate wavelength irradiation. In an alternative embodiment of the present invention, a chemical reaction initiates the phase change from liquid to solid which retains the suture in the container.

DETAILED DESCRIPTION OF THE INVENTION

Figure 1:
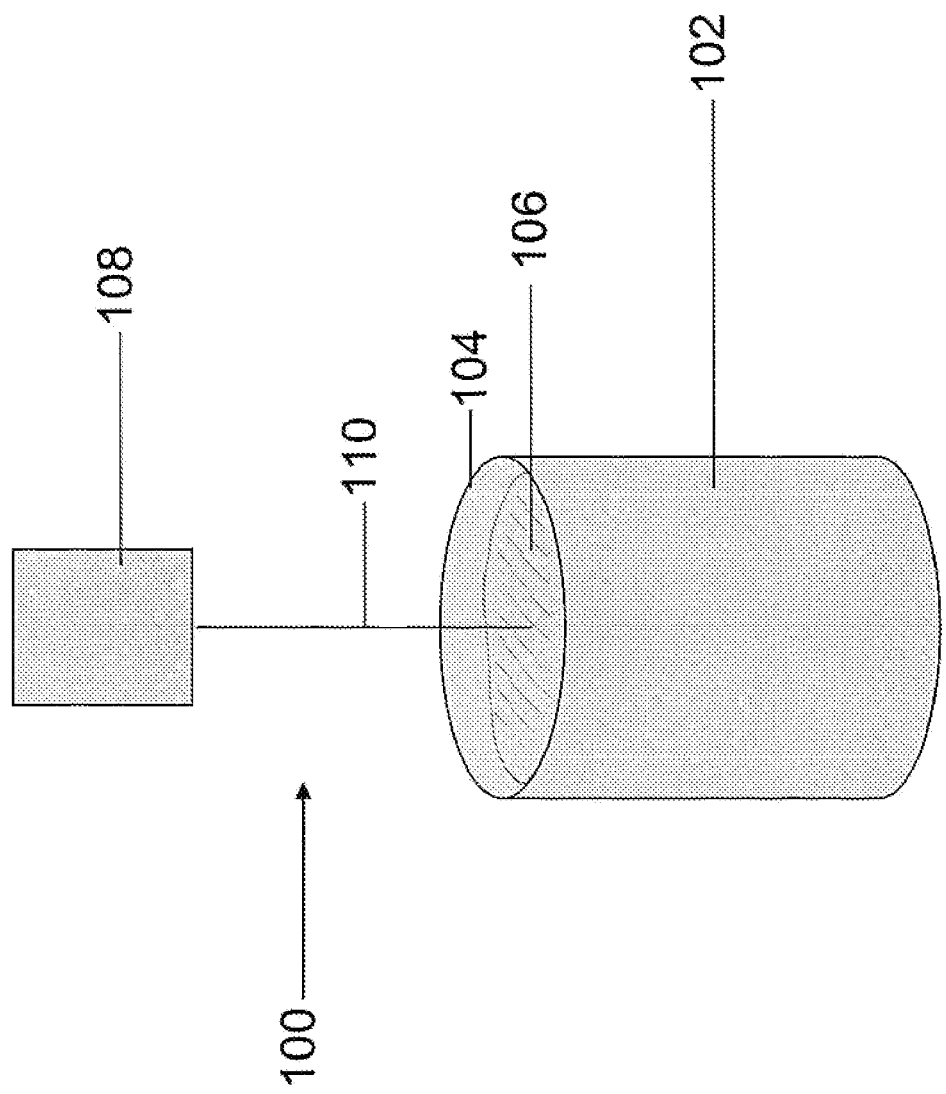
FIG. 1 is a perspective view of an embodiment of a testing device of the present invention.

Bioabsorbable sutures can be made of materials which are broken down in tissue after a given period of time, which depending on the material can be from ten days to eight weeks (and in some cases, such as with sutures made of recombinant materials, twenty weeks or more). The sutures are used therefore in many of the internal tissues of the body. In most cases, three weeks is sufficient for the wound to close firmly. At that time the suture is not needed any more, and the fact that it disappears is an advantage, as there is no foreign material left inside the body and no need for the patient to have the sutures removed. In rare cases, bioabsorbable sutures can cause inflammation and be rejected by the body rather than absorbed. Bioabsorbable sutures were first made from the intestines of mammals. For example, gut sutures can be made of specially prepared bovine or ovine intestine, and may be untreated (plain gut), tanned with chromium salts to increase the suture persistence in the body (chromic gut), or heat-treated to give more rapid absorption (fast gut). Concern about transmitting diseases such as bovine spongiform encephalopathy, has resulted in the gut being harvested from stock which have been tested to determine that the natural polymers used as suture materials do not carry viral diseases. Bioabsorbable sutures can be made of synthetic polymer fibers, which may be monofilaments or braided.

Synthetic sutures offer numerous advantages over gut sutures, notably ease of handling, low cost, low tissue reaction, consistent performance and non-toxicity. Various blends of polyglycolic acid, lactic acid or caprolactone are common as synthetic bio-absorbable sutures. Examples of bioabsorbable sutures include sutures made from catgut (collagen), kangaroo tendons, glycolic acid polymers, l-lactic acid polymers, d-lactic acid polymers, trimethylene carbonate polymers, para-dioxanone polymers, epsilon-caprolactone polymers, polyhydroxyalkanoate polymers as well as copolymers using any combination of these materials as well as other chemically similar materials.

Non-bioabsorbable sutures can be made of materials which are not metabolized by the body, and are used therefore either on skin wound closure, where the sutures can be removed after a few weeks, or in some inner tissues in which absorbable sutures are not adequate. This is the case, for example, in the heart and in blood vessels, whose rhythmic movement requires a suture which stays longer than three weeks, to give the wound enough time to close. Other organs, like the bladder, contain fluids which make absorbable sutures disappear in only a few days, too early for the wound to heal. There are several materials used for non-bioabsorbable sutures. The most common is a natural fiber, silk. Other non-bioabsorbable sutures can be made of artificial fibers, like polypropylene, polyester or nylon; these may or may not have coatings to enhance the suture performance characteristics. Likewise, examples of non-bioabsorbable sutures include sutures made from polyamide, polybutesters, polyetherester, polyetheretherketone, polyethylene, polyethylene terephthalate, polyurethane, polypropylene, polytetrafluoroethylene, metals, metal alloys, cotton and silk.

It is important to understand that the classification of bioabsorbable and non-bioabsorbable sutures is not absolute. For example, most polyesters are non-bioabsorbable (such as polyethylene terephthalate) except that some polyesters (such as those made from polyglycolic acid, polylactic acid, or polyhydroxyalkanoates) are bioabsorbable. Similarly, silk is generally considered as a non-bioabsorbable material, but over a long period of time (e.g., 10 to 25 years), the body can break-down silk sutures implanted in the body.

Polyhydroxyalkanoic acids (PHAs) are carbon and energy reserve polymers produced in some bacteria when carbon sources are plentiful and other nutrients, such as nitrogen, phosphate, oxygen, or sulfur are limiting. Naturally occurring PHAs are composed of monomers that range from 3 to 14 carbons. PHAs can be made by genetically engineering microorganisms including *Ralstonia eutropha* (*R. eutropha*) (formerly *Alcaligenes eutrophus*) or *Escherichia coli* (*E. coli*) bacteria to biologically synthesize the desired PHAs. Bioabsorbable linear polyesters such as PHA made from bacteria can be produced through fermentation using sugars and or lipids as the carbon and energy sources. Some PHA polyesters have physical properties similar to those of polypropylene, making them an alternative source of plastic which is biodegradable and can be formed from renewable resources. Homopolymers composed of 3-hydroxybutyric acid (PHB) are very brittle. In contrast PHAs possessing longer carbon backbones including poly-3-hydroxyhexanoate (PHH) and poly-3-hydroxyoctanoate (PHO) result in a more flexible polymer. As a result, homopolymers of PHH and PHO are more attractive for use in making sutures.

PHB was first discovered in 1927 at the Pasteur Institute in Paris. In a natural state, PHB exists as a noncrystalline polymer, but the extraction procedures convert it to be high crystalline and brittle, which limited its application. PHB can be chemically synthesized by catalytic ring-opening polymerization of 3-butyrolactone, but is industrially biosynthesized from renewable resources by bacteria action on sugar of wheat or beet.

PHB is synthesized from acetyl-coenzyme A (CoA) in a three-step pathway. The first reaction involves a PHA-specific 3-ketothiolase, encoded by phaARe, that condenses two acetyl-CoA molecules into acetoacetyl-CoA. The second reaction, which is the reduction of acetoacetyl-CoA to d-(−)-3-hydroxybutyryl-CoA, is catalyzed by an NADPH-dependent acetoacetyl-CoA reductase, encoded by phaBRe. The last reaction is catalyzed by PHA synthase, which is the product of the phaCRe gene. In this reaction, d-(−)-3-hydroxybutyrl-CoA is linked to an existing PHA molecule by the formation of an ester bond. In addition to the three-step pathway just described, different (d)-3-hydroxyacyl-CoA substrates may be used by the PHA synthase to construct PHAs of different monomeric compositions. These alternative substrates for PHA synthase could be provided by intermediates of other metabolic pathways, such as the fatty acid oxidation pathway, the fatty acid synthesis pathway, the methylmalonyl-CoA pathway, and the isoleucine-valine degradation pathway.

*Chromobacterium violaceum* (*C. violaceum*) is known to accumulate polymers composed primarily of PHB and PHBV and can produce a homopolymer of 3HV when grown on valerate (see Kolibachuk, D. et al., Appl. Environ Microbiol. (1999) 65, pp 3561-3565, entitled "Cloning, Molecular Analysis, and Expression of the Polyhydroxyalkanoic Acid Synthase (phaC) Gene from *Chromobacterium violaceum*" which is expressly incorporated by reference in its entirety). *R. eutropha* harboring a 6.3-kb BamHI fragment from *C. violaceum*, containing phaCCv and the polyhydroxyalkanoic acid (PHA)-specific 3-ketothiolase (phaACv) produced significant levels of PHA synthase and 3-ketothiolase. *C. violaceum* accumulated recombinant PHB (rPHB) or recombinant PHBV (rPHBV) when grown on a fatty acid carbon source. In contrast, *R. eutropha*, harboring the phaCCv fragment, accumulated rPHB, rPHBV and the rPHBH when even-chain-length fatty acids were utilized as the carbon source. The Kolibachuk report verifies the ability of the synthase from *C. violaceum* to incorporate other rPHA monomers to form a variety of copolymers.

PHBV copolymers have molecular weights of about 500,000 g/mol and are 100% isotactic. The stereoregularity is superior to that of the chemically synthesized polymers of comparable molecular weights by ring-opening copolymerization of lactones. The flexibility and tensile strength of the copolymer depend on the HV content. The PHBV copolymers show piezo-electric properties, are stable in water and alcohol and are weakly resistant to acids and alkalis. The PHBV copolymer degrades faster than PHB. The mechanical properties of different composition PHBV's are given in Table 1.

TABLE 1

Properties of PHBV copolymers.

| | HB: HV content | | |
|---|---|---|---|
| | 100% HB | 92% HB, 8% HV | 88% HB, 12% HV |
| Tg/° C. | 1 | −1 | 2 |
| Tm/° C. | 179 | 153 | 144 |
| TS (MPa) | 40 | 28 | 23 |
| % Elongation | 6-8 | 20 | 352 |
| Modulus (GPa) | 3.5 | 2 | 1.4 |
| Crystallinity | 60-80 | 5 | |

Thus, the compositions of the polymers produced from bacteria can be varied depending on the substrate specificity of the PHA synthase, the carbon source on which the bacterium is grown, and the metabolic pathways involved in the utilization of the carbon source. During the 1980s, ICI/Zeneca researchers reported transferring three genes responsible for PHB production in *R. eutropha* to *E. coli* resulting in the recombinant bacterial synthesis of PHB. In 1996 Monsanto began marketing a copolymer composed of poly(3-hydroxybutyrate-co-3-hydroxyvalerate) (PHBV) under the trademark name BIO-POL®. In 1992 a team at the Department of Energy Plant research lab at Michigan State University took two genes from PHB-making bacteria and inserted them directly into *Arabidopsis thaliana* (cruciferae, 'Thale cress') and the plants accumulated PHB up to 14% by dry weight as granules within the plastids, with no deleterious effect on growth. The maximum thickness of rPHBV is 1 mm which would allow a variety of different size sutures up to and including orthopedic sutures.

Careful control of the starting materials and the choice of production organisms enables the production of an entire PHA family with different properties, such as the copolyester with random combinations of β-hydroxybutyrate and β-valerate. Such copolyesters have much better mechanical properties (that are similar to those of Polypropylene) than those of the homopolymers. Some examples of PHAs with longer alkyl groups produced by bacteria in the form of copolymers, useful as thermoplastic elastomers, include poly((3-hydroxybutyrate-co-3-hydroxypropionat) (PHBP), poly(3-hydroxybutyrate-co-3-hydroxyhexnoate) (PHBH), and poly (3-hydroxybutyrate-co-4-hydroxybutyrate) (PHBB). A number of PHB-based plastics have been developed for packaging application (U.S. Pat. Nos. 5,231,148 and 5,625,029 which are expressly incorporated by reference in their entireties). The mechanical properties of some of these copolymers are listed in Table 2.

TABLE 2

Properties of PHB copolymers

| | Copolymers | | | |
|---|---|---|---|---|
| | PHB/PCL | PHB/PBA | PHBV | PHB/PEO |
| Composition | 77/23 | 75/25 | 74/26 | 75/25 |
| Tg/° C. | 1/— | −4/−68 | 8 | −21 |
| Tm/° C. | 178/59 | 175/55 | 178 | 178/61 |
| TS (MPa) break | 21 | 32 | | |
| % Elongation | 9 | 7 | 0 | 0 |
| Modulus (MPa) | 730 | 1050 | | |

The exciting potential of production of biodegradable plastics using abundant renewable resources (corn, soybean, etc.) is apparent from the spate of recent joint-ventures as well as business purchases by big multinational commodity firms, like Monsanto and Cargill. Monsanto engineered cress plants and oil-seed rape, manipulating the plant's production of amino acids and fatty acid in order to produce the plastic PHBV. Cargill Dow Polymers recently developed lactic acid production technology based on corn starch that will enable low cost production of PLA. Among others, both BASF and Eastman Chemical have developed biodegradable aliphatic/aromatic co-polyester that may be produced in existing polyester facilities. Some industrial resins are summarized in Table 3.

TABLE 3

Commercial Industrial Resins.

| Category | Polymer | Trade Name |
|---|---|---|
| Biosynthetic | PHBV | Biopol (Monsanto) |
| | Poly (lactide) | EcoPla NatureWork (Cargill Dow) |
| | | Lacea (Mitsui Chemicals) |
| | Pullulan | Pullulan (Hayashihara) |
| Chemo synthetic | Poly (butylene succinate) | Bionolle 1000 (Showa Highpolymer) |
| | Poly (butylene succinate adipate) | Bionolle 3000 (Showa Highpolymer) |
| | Poly (butylene succinate terephthalate) | Biomax (DuPont) |
| | Copolyester | Ecoflex (BASF) |
| | Copolyester | Eastar Bio (Eastman Chemicals) |
| | Polycaprolactone | Tone (Union Carbide) |

TABLE 3-continued

Commercial Industrial Resins.

| Category | Polymer | Trade Name |
|---|---|---|
| | Poly (vinyl alcohol) | Airvol (Air Products and Chemicals) |
| | Poly (ester amide) | BAK (Bayer) |
| Natural | Cellulose acetate | EnviroPlastic-Z (Planet Polymer) |
| | Starch-based polycaprolactone | Bioplast (Biotec) |
| | Starch-based plastic | Mater-Bi (Novamont) |

A basic requirement of medical devices is that the devices are nonpyrogenic, i.e., that the products do not induce fever reactions when administered to patients. The presence of bacterial endotoxin in a bacterially expressed rPHA is by far the largest concern of manufacturers in achieving nonpyrogenation. The U.S. Food and Drug Administration (FDA) requires the endotoxin content of medical devices not exceed 20 USP endotoxin units (EU) per device. Endotoxin levels need to be even lower for some specific applications. While this is particularly relevant for rPHAs derived by fermentation of gram-negative bacteria there are also concerns for rPHAs derived from plants. Therefore, in developing rPHAs for use as self-retaining sutures, the rPHAs specific endotoxin content requirements can be analyzed to determine whether the sutures exceed the FDA limits.

'Self-retaining suture' refers to a suture that may not require a knot in order to maintain its position into which it is deployed during a surgical procedure. Such self-retaining sutures generally include a retaining element or tissue retainer.

'Tissue retainer' refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction (i.e. the retainers lie flat when pulled in the deployment direction; and open or "fan out" when pulled in a direction contrary to the deployment direction). As the tissue-penetrating end of each retainer faces away from the deployment direction when moving through tissue during deployment, the tissue retainers should generally avoid catching or grabbing tissue during this phase. Once the self-retaining suture has been deployed, a force exerted in another direction (often substantially opposite to the deployment direction) causes the retainers to be displaced from their deployment positions (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. By way of example only, tissue retainer or retainers can include hooks, projections, barbs, darts, extensions, bulges, anchors, protuberances, spurs, bumps, points, cogs, tissue engagers, tractions means, surface roughness, surface irregularities, surface defects, edges, facets and the like.

Various forms of rPHBV are characterized by melting points of between approximately 130° C. to approximately 180° C., and extensions-to-break strengths of 8 to 42% (see Zeneca Promotional Literature, Billingham, UK 1993; and U.S. Patent Application No.: 20020106764 to A. Steinbuchel, et al. entitled "Sulfur containing polyhydroxyalkanoate compositions and method of production", which are hereby expressly incorporated by reference in their entireties. Forms of rPHBV are also some of the strongest bioabsorbable fibers known, offering up to 50% greater tensile strength than glycolic acid polymer monofilament bioabsorbable sutures. As a result, rPHBV is both tougher than and more flexible than PHB. Further, rPHBV has an absorption rate and degradation profile that is compatible with human tissue repair and replacement applications. However, unlike other biopolymers such as collagen and hyaluronate, PHBV is a thermoplastic. As such rPHBV can be fabricated into virtually any shape or form including fibers, films, tubes, foams, textiles, microspheres, and molded constructs, using a wide range of conventional melt and solvent processing techniques. Another PHA with attractive physical properties is a copolymer of 3-hydroxybutyrate-and-3-hydroxyhexanoate (rPHBH).

In an embodiment of the invention, sutures can be made from biomaterials such as recombinant polyhydroxyalkanoate (rPHA) polymers synthesized in bacterial expression systems. In an embodiment of the invention, a homopolymer material synthesized by a recombinant bacterial expression system can be used as a material for making a self-retaining suture. In an embodiment of the present invention, rPHA homopolymers can be used as a monofilament for making a self-retaining suture. In an embodiment of the present invention, rPHA homopolymers can be used to form multi-filaments for making a self-retaining suture. In various embodiments of the invention, rPHA homo polymers including poly-3-hydroxybutyrate (PHB), poly-4-hydroxybutyrate (P4HB), poly-3-hydroxyvalerate (PHV), poly-3-hydroxypropionate (PHP), poly-2-hydroxybutyrate (P2HB), poly-4-hydroxyvalerate (P4HV), poly-5-hydroxyvalerate (P5HV), poly-3-hydroxyhexanoate (PHH), poly-3-hydroxyoctanoate (PHO), poly-3-hydroxyphenylvaleric acid (PHPV) and poly-3-hydroxyphenylhexanoic acid (PHPH) can be used as materials for making self-retaining sutures. In an embodiment of the present invention, rPHA homopolymers having melting points (Tm) ranging between approximately 40° C. to approximately 180° C. can be used as materials for making self-retaining sutures.

In an alternative embodiment of the invention, a rPHA block or random copolymer material synthesized in a bacterial expression system can be used for making a self-retaining suture. In an embodiment of the present invention, rPHA copolymers can be used as a monofilament for making a self-retaining suture. In an alternative embodiment of the present invention, rPHA block and/or random copolymers can be used to form multi-filaments for making a self-retaining suture. Roughly 100 different types of rPHAs have been produced by fermentation methods. A number of these rPHAs contain functionalized pendant groups such as esters, double bonds, alkoxy, aromatic, halogens, and hydroxyl groups which can be further crosslinked, reacted, derivatized or undergo non covalent interactions to modify the properties of the rPHA. In addition to transgenic systems for producing rPHAs in both microorganism and plants, enzymatic methods for PHA synthesis are known (see Steinbuchel and Valentin, FEMS Microbiol. Lett., 128:219 28 (1995) and Williams and Peoples, CHEMTECH, 26:38 44 (1996), which are both hereby expressly incorporated by reference in their entireties). In various embodiments of the invention, rPHA copolymers including poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxyhexanoate) (PHB4H), poly(3-hydroxybutyrate-co-6-hydroxyhexanoate) (PHB6H), poly(3-hydroxybutyrate-co-3-hydroxyoctanoate) (PHBO), poly(3-hydroxybutyrate-co-3-hydroxyphenylvaleric acid) (PHBPV), poly(3-hydroxybutyrate-co-3-hydroxyphenylhexanoic acid) (PHBPH), poly(4-hydroxybutyrate-co-3-hydroxyvalerate) (P4HBV), poly(4-hydroxybutyrate-co-3-hydroxyhexanoate) (P4HBH), poly(4-hydroxybutyrate-co-4-hydroxyhexanoate) (P4HB4H), poly(4-hydroxybutyrate-co-6-hydroxyhexanoate) (P4HB6H), poly(4-hydroxybutyrate-co-3-hydroxyoctanoate) (P4HBO), poly(4-hydroxybutyrate-co-3-hydroxyphenylvaleric acid) (P4HBPV), poly(4-hydroxybutyrate-co-3-hydroxyphenylhexanoic acid) (P4HBPH), poly(3-hydroxyvalerate-co-3-hydroxyhexanoate) (PHVH), poly(3-hydroxyvalerate-co-4-hydroxyhexanoate) (PHV4H), poly(3-hydroxyvalerate-co-6-hydroxyhexanoate) (PHV6H), poly(3-hydroxyvalerate-co-3-hydroxyoctanoate) (PHVO), poly(3-hydroxyvalerate-co-3-hydroxyphenylvaleric acid) (PHVPV), poly(3-hydroxyvalerate-co-3-hydroxyphenylhexanoic acid) (PHVPH), poly(3-hydroxyvalerate-co-3-hydroxyphenylvaleric acid) (PHVPV), poly(3-hydroxyvalerate-co-3-hydroxyphenylhexanoic acid) (PHVPH), poly(3-hydroxypropionate-co-3-hydroxyvalerate) (PHPV), poly(3-hydroxypropionate-co-3-hydroxyhexanoate) (PHPH), poly(3-hydroxypropionate-co-4-hydroxyhexanoate) (PHP4H), poly(3-hydroxypropionte-co-6-hydroxyhexanoate) (PHP6H), poly(3-hydroxypropionate-co-3-hydroxyoctanoate) (PHPO), poly(3-hydroxypropionate-co-3-hydroxyphenylvaleric acid) (PHPPV), poly(3-hydroxypropionate-co-3-hydroxyphenylhexanoic acid) (PHPPH), poly(2-hydroxybutyrate-co-3-hydroxyvalerate) (P2HBV), poly(2-hydroxybutyrate-co-3-hydroxyhexanoate) (P2HBH), poly(2-hydroxybutyrate-co-4-hydroxyhexanoate) (P2HB4H), poly(2-hydroxybutyrate-co-6-hydroxyhexanoate) (P2HB6H), poly(2-hydroxybutyrate-co-3-hydroxyoctanoate) (P2HBO), poly(2-hydroxybutyrate-co-3-hydroxyphenylvaleric acid) (P2HBPV), poly(2-hydroxybutyrate-co-3-hydroxyphenylhexanoic acid) (P2HBPH), poly(4-hydroxyvalerate-co-3-hydroxyvalerate) (P4HVV), poly(4-hydroxyvalerate-co-3-hydroxyhexanoate) (P4HVH), poly(4-hydroxyvalerate-co-4-hydroxyhexanoate) (P4HV4H), poly(4-hydroxyvalerate-co-6-hydroxyhexanoate) (P4HV6H), poly(4-hydroxyvalerate-co-3-hydroxyoctanoate) (P4HVO), poly(4-hydroxyvalerate-co-3-hydroxyphenylvaleric acid) (P4HVPV), poly(4-hydroxyvalerate-co-3-hydroxyphenylhexanoic acid) (P4HVPH), poly(5-hydroxyvalerate-co-3-hydroxyvalerate) (P5HVV), poly(5-hydroxyvalerate-co-3-hydroxyhexanoate) (P4HVH), poly(5-hydroxyvalerate-co-4-hydroxyhexanoate) (P5HV4H), poly(5-hydroxyvalerate-co-6-hydroxyhexanoate) (P5HV6H), poly(5-hydroxyvalerate-co-3-hydroxyoctanoate) (P5HVO), poly(5-hydroxyvalerate-co-3-hydroxyphenylvaleric acid) (P5HVPV), poly(5-hydroxyvalerate-co-3-hydroxyphenylhexanoic acid) (P5HVPH), can be used as materials for making self-retaining sutures. In an embodiment of the present invention, rPHA copolymers have melting points ranging between approximately 40° C. to approximately 180° C.

In a further alternative embodiment, a rPHA homo polymer is used as the monofilament base material for making a self-retaining suture. In an embodiment of the present invention, a monofilament can be coated with a rPHA copolymer, for use as a self-retaining suture. In an embodiment of the invention, self-retaining sutures can be made from rPHBV copolymers. In an alternative embodiment of the invention, self-retaining sutures can be made from rPHBH copolymers. In an embodiment of the present invention, rPHA copolymers have varied elastomeric and/or thermoplastic properties compared with the corresponding PHA synthetic copolymer. In an embodiment of the present invention, rPHA copolymers from *R. eutropha* have varied elastomeric and/or thermoplastic properties compared with the corresponding synthetic polymer. In an embodiment of the invention, a self-retaining suture material made from a monofilament or multifilament coated with a rPHA homopolymer can have a melting point ranging between approximately 40° C. to approximately 180° C. In an embodiment of the invention, a self-retaining suture material made from a monofilament or multifilament coated with a rPHA block or random copolymer can have a melting point ranging between approximately 40° C. to approximately 180° C.

In an embodiment of the present invention, rPHA homopolymers are blended with rPHA block and/or random copolymers to produce material for making self-retaining sutures. In an alternative embodiment of the present invention, rPHA homopolymers are cross-linked with rPHA block and/or random copolymers to produce material for making self-retaining sutures. In another embodiment of the present invention, rPHA homopolymers are chemically reacted with rPHA block and/or random copolymers to produce material for making self-retaining sutures.

Polyglycolic acid (PGA) is the simplest aliphatic polyester polymer. The monomer, glycolic acid, occurs naturally in sugarcane syrup and in the leaves of certain plants, but can also be synthesized chemically. Ring-opening polymerization of the cyclic dimmer, glycolide, yields high molecular weight polymers. PGA has a high crystallinity (45-55%) that leads to its insolubility in water and most organic solvents. Glycolic acid has been copolymerized with other monomers to reduce the crystallinity and stiffness of the resulting copolymers. These copolymers, such as poly(glycolide-co-1, 3-trimethylene carbonate) (TMC/PGA) trade name polyglyconate) (U.S. Pat. No. 5,695,879 which is expressly incorporated by reference in its entirety), poly(lactide-co-glycolide) (PLAGA) (U.S. Pat. No. 4,960,866 which is expressly incorporated by reference in its entirety), poly(glycolide-co-ethylene oxide) (PGA/PEO) and poly(glycolide-co-p-dioxanone) (PGA/PDO), are used in medical devices or drug delivery systems. PGA undergoes enzymatic and hydrolytic degradation.

Poly-lactic acid (PLA) is the most widely used biodegradable polyester. PLA polymers are not only used as implants in human bodies, but can also replace petroleum-based polymers in many application items. The monomer lactic acid is found in blood and muscle tissue as a product of the metabolic process of glucose. High molecular weight polylactide is obtained by ring-opening polymerization of the cyclic dimer of lactic acid. Lactic acid can be derived by fermentation of starchy products such as corn, and then converted to PLA through low-cost, high-yield catalytic polymerization (U.S. Pat. No. 5,981,694 which is expressly incorporated by reference in its entirety). Due to the asymmetrical β carbon of lactide acid, D and L stereoisomers exist, and the resulting polymer can be either isomeric (D, L) or racemic DL. Petrochemical PLA is a mixture of D- and L-stereoisomer (50/50), whereas the fermentation of renewable resources forms uniquely L-lactic acid. Proteinase K preferentially degrades L-L, L-D and D-L bonds as opposed to D-D linkages. PLA is water resistant, unstable in acidic and alkali solutions, soluble in halogenated hydrocarbons, ethyl acetate, THF and dioxane. Poly(L-lactic acid) (PLLA) is semi-crystalline, and suitable for applications such as orthopedic fixings and sutures (U.S. Pat. No. 5,567,431 which is expressly incorporated by reference in its entirety). Poly(DL-lactic acid) (PDLLA) is amorphous, degrades more rapidly, and is more attractive as a drug delivery system. PLA degrades via composting within three weeks, by first undergoing a hydrolysis reaction and then a microbial decomposition during which carbon dioxide and water are generated. PLA is more hydrophobic than PGA and hydrolyzed more slowly in vivo.

Polycaprolactone (PCL) is a water stable, hydrophobic and semi-crystalline polymer. The preparation of PCL and its copolymers from ε-caprolactone can be effected by different mechanisms including anionic, cationic, coordination and radical polymerization. PCL can be hydrolyzed by fungi or through chemical hydrolysis. Chemical degradation of PCL is slower than poly(α-hydroxyalkanoic acids). Since the degradation of PCL needs about 2 years, copolymers have been developed for applications demanding an accelerated degradation rate. PCL possesses good mechanical properties, is more hydrophobic than and compatible with many polymers. Properties of some industrial PCL products can be found in Table 4. PCL as a thermoplastic finds many applications in packaging, adhesives, controlled release of drugs, fertilizers, pesticides, polymer processing, medical devices (see U.S. Pat. No. 5,753,781 to J. D. Oxman et al. entitled "Blended polycaprolactone thermoplastic molding composition"), and synthetic wound dressings.

TABLE 4

Comparison of Properties of PCL products.

| Trade name | CAPA 650 | CAPA 680 | Tone p767 | Tone p787 |
|---|---|---|---|---|
| Producer | Solvay Interox | Solvay Interox | Union Carbide | Union Carbide |
| Tg/° C. | −60 | −60 | −60 | −60 |
| Tm/° C. | 60-62 | 60-62 | 60 | 60 |
| TS (MPa) | 21-26 | 39-42 | | |
| % Elongation | >700 | 920 | 600-1000 | 750-1000 |
| Yield stress (GPa) | 17.2-17.5 | 14-16 | | |
| Fracture stress | 29+/−11 | 54 | | |
| Crystallinity | 56 | 56 | | |

Poly(p-dioxanone) (PDO), also referred as poly(oxyethylene glycoate) and poly(ether ester) is formed by the ring-opening polymerization of p-dioxanone (U.S. Pat. No. 4,490,326). The polymer must be processed at the lowest possible temperature to prevent depolymerization back to monomer. The monofilament loses 50% of its initial breaking strength after 3 weeks and is absorbed within 6 months, providing an advantage over other products as a suture for slow-healing wounds.

In an embodiment of the present invention, one or more rPHAs are coated or otherwise blended with one or more non-recombinant bioabsorbable polymers to produce material for making self-retaining sutures, where the other bioadsorbable polymers include PGA, PLLA, poly-d-lactic acid, polytrimethylene carbonate, PDO and PCL. By coating the suture first polymer filament with a second polymer, a tissue specific reaction can be induced by the exterior coating. In an embodiment of the present invention, one or more rPHAs are chemically cross-linked with one or more other bioabsorbable polymers to produce material for making self-retaining sutures, where the other bioadsorbable polymers include polyglycolic acid, poly-l-lactic acid, poly-d-lactic acid, polytrimethylene carbonate, PDO, PCL, polyurethane, protamine, polylysine and lipids. In an embodiment of the invention, the filament material is able to induce a tissue specific reaction and the coating is not able to induce a tissue specific reaction. By placing the coating of the filament and then inserting tissue retainers, the tissue specific reaction is localized on the suture tissue retainers which thereby directs the collagen deposition on or surrounding the tissue retainers to strengthen the tissue retainers insertion into the tissue. In an embodiment of the present invention, collagen fibers are coated onto a bioabsorbable self-retaining monofilament to increase the tissue reaction and improve the post operative self-retaining holding strength. In an alternative embodiment of the present invention, a bioabsorbable tissue retainer suture coating further comprises small collagen fibers blended into a bioadsorbable self-retaining monofilament to increase the tissue reaction and improve the post operative self-retaining holding strength. In an embodiment of the present invention, small PGA fibers, regular shaped PGA spheres and irregular shaped PGA spheres are incorporated into a bioabsorbable self-retaining monofilament polymer to increase the tissue reaction and improve the post operative self-retaining holding strength. In various embodiments of the present invention, a bioabsorbable self-retaining suture coating further includes one or more of small PGA fibers, regular shaped PGA spheres and irregular shaped PGA spheres into a bioabsorbable monofilament polymer with tissue retainers to increase the tissue reaction and improve the post operative self-retaining holding strength.

PHAs can be treated with a chemical reagent to cleave ester linkages in the polymer backbone resulting in the formation of free hydroxyl and carboxylic acid groups, thereby altering the local structure, the local and overall charge and providing reactive functional groups for subsequent modification and/or coordination. This chemical treatment can also promote or reduce cellular adhesion by the polymer. Reagents which can be used to cleave the polymer backbone include water, bases, acids, nucleophiles, electrophiles, plasma, and metal ions. Hydrolysis of the esters can also be performed enzymatically using esterases or, alternatively, bonds can be cleaved by ultra violet or infrared irradiation and/or the application of heat. These modifications can be carried out homogeneously if the PHA is in solution. Alternatively, if the PHA is an extruded solid, then the modifications can be limited to the exposed polymer surface area. This allows surface properties of the PHAs to be modified without altering the overall mechanical properties of the underlying polymer. Certain PHAs with exposed unsaturated groups can be oxidized to diols, alcohols, aldehydes, and acids. Bioactive species can also be covalently attached to the exposed functional groups of PHAs. In an embodiment of the present invention, one or more rPHAs are chemically reacted with one or more non-recombinant bioabsorbable polymers to produce material for making self-retaining sutures, where the non-recombinant bioadsorbable polymers include polyglycolic acid, poly-l-lactic acid, poly-d-lactic acid, polytrimethylene carbonate, PDO, PCL, protamine, polylysine and lipids.

Bioactive species can also be ionically attached to the exposed functional groups of PHAs. For example, the PHAs which include a carboxylic acid group can form an ionic bond with amine groups present on materials such as protamine and polylysine or a hydrogen bond with collagen or polyurethane or with other materials. Such modifications can, for example, change surface properties like hydrophobicity and surface charge of the polymers. Other examples of molecules which can modify PHAs non-covalently are lipids. In an embodiment of the present invention, one or more rPHAs are non covalently modified with one or more native bioabsorbable polymers to produce material for making self-retaining sutures, where the native bioadsorbable polymers include polyglycolic acid, poly-l-lactic acid, poly-d-lactic acid, polytrimethylene carbonate, PDO, PCL, protamine, polylysine and lipids.

Synthetic PHAs generally result in minimal tissue reaction when implanted in vascularized tissue eliciting a minimal inflammatory response. However, other (bioadsorbable and non-bioadsorbable) polymers can cause a tissue reaction when implanted into the muscle of an animal. For example, inflammation can be caused by a reaction to foreign proteins present in some natural bioabsorbable sutures. PHAs generated from recombinant bacterial systems may induce an inflammatory response and adverse tissue reaction. The tissue response would be initiated within a lower limit of 1-3 hours from insertion of the suture to an upper limit of several days after insertion. The tissue response would endure for a period of a lower limit of 1-3 hours from the time of insertion of the suture to an upper limit of several days after insertion However, depyrogenated PHAs implanted in vivo do not result in an acute inflammatory reaction. The inflammation can amplify scarring and for this reason is not desirable. Alternatively, tissue reactions can also induce collagen deposition at the suture site, which can improve the holding strength of a self-retaining suture. Parallel increases in immune activation, transforming growth factor (TGF) positive regulatory T (Treg) cells and collagen type I deposition have been observed consistent with early immune activation eliciting collagen deposition. Collagen deposition can also be induced through chemical agents such as silica (see E. Cosini et al., Mechanisms of Ageing and Development (2004), 125: 145-146, in '2002 International Conference on Immunology and Aging', entitled "Resistance to silica-induced lung fibrosis in senescent rats: role of alveolar macrophages and tumor necrosis factor-$\alpha$ (TNF)") or via stimulation of connective tissue growth factor (see Edwin C. K. Heng et al., J Cell Biochem. (2006) 98: 409-420 entitled "CCN2, Connective Tissue Growth Factor, Stimulates Collagen Deposition By Gingival Fibroblasts Via Module 3 And $\alpha$-6 And $\beta$-1 Integrins"). In an embodiment of this invention, the increased tissue reaction can cause an increased amount of collagen formation which can improve the self-retaining suture tissue holding strength post operatively. By coating the suture first polymer filament with a second polymer which causes a tissue specific reaction, a tissue reaction can be induced. Further, by adjusting the thickness of the second polymer coating the time duration of the tissue reaction can be adjusted without sacrificing other properties of the suture such as strength. In an alternative embodiment of this invention, the increased tissue reaction can cause relatively faster collagen formation which can improve the self-retaining suture tissue holding strength post operatively.

In an embodiment of the present invention, a monofilament with a polyglycolic acid (PGA) outer layer is co-extruded with a different bioabsorbable polymer inner layer for generating a self-retaining suture. The purpose of the PGA outer layer is to increase a tissue reaction induced by the self-retaining suture in vivo. This increased tissue reaction can improve the self-retaining suture holding strength (e.g., by increasing the formation of collagen tissue growth). In an embodiment of the present invention, the configurations of the inner layer to the outer layer can be spherical-coaxial. In an embodiment of the present invention, the configurations of the inner layer to the outer layer can be pie shaped-coaxial. A pie shaped-coaxial filament can be advantageous to allow the monofilament to interact with other filaments along the length of the non outer layer exposed surface of the filament, while along the remaining surface of the filament where the outer layer is present tissue retainers can be inserted. In an embodiment of the invention, the outer layer can be in a preferred form for introducing tissue retainers. In an alternative embodiment of the present invention, the monofilament can interact with other filaments along the length of the outer layer exposed surface of the filament, while along the remaining surface of the filament where the outer layer is not present tissue retainers can be inserted. In an embodiment of the present invention, the outer layer can be applied as a thin coating. In various embodiment of the present invention, the outer PGA layer comprises 50% or greater glycolide content. In an embodiment of the present invention, the tissue retainers are introduced into the surface of one or more filaments containing PGA material. In an alternative embodiment of the present invention, the tissue retainers are introduced into the surface of one or more filaments containing PHA material.

In an embodiment of the present invention, recombinant expressed bioabsorbable polymers can be used to make small self-retaining monofilament filaments such monofilaments similar in size to U.S.P. 7/0, 8/0, 910, 10/0 and 11/0 suture sizes. In an embodiment of the present invention, rPHAs can be used to make small self-retaining monofilament filaments such monofilaments similar in size to the U.S.P. 7/0, 8/0, 910, 10/0 and 11/0 suture sizes. In a different embodiment of the present invention, recombinant expressed bioabsorbable polymers blended with non-bioabsorbable polymers can be used to make small self-retaining monofilaments similar in size to the U.S.P. 7/0, 8/0, 910, 10/0 and 11/0 suture sizes. In an alternative embodiment of the present invention, recombinant expressed bioabsorbable polymers coated with non-recombinant expressed bioabsorbable polymers can be used to make small self-retaining monofilaments similar in size to the U.S.P. 7/0, 8/0, 910, 10/0 and 11/0 suture sizes. In another embodiment of the present invention, recombinant expressed bioabsorbable polymers coated with non-bioabsorbable polymers can be used to make small self-retaining monofilaments similar in size to the U.S.P. 7/0, 8/0, 910, 10/0 and 11/0 suture sizes.

In an alternative embodiment of the present invention, bioadsorbable monofilaments are braided together to give a bioabsorbable self-retaining suture. In an embodiment of the present invention, filament sizes can be equivalent to U.S.P. monofilament 9/0 and 10/0, but both larger and smaller filament sizes are also envisioned. In an embodiment of the present invention, more than one filament size can be used to construct the multifilament braid. In an embodiment of the present invention, a braided suture can be made with and without a braid core. In an embodiment of the present invention, the braided suture core can be a single monofilament core, a collection of parallel multi-filaments (i.e., a core comprising many small monofilament fibers having little or no twist), twisted multifilament core, and/or a braided multifilament core. In an embodiment of the present invention, both self-retaining and non-self-retaining material can be used for the suture core. In an embodiment of the invention, a suture made from a braid of non-self-retaining filaments and tissue retainers can subsequently be introduced.

In an embodiment of the present invention, the self-retaining braided suture is braided with tissue retainers only in one direction. In an alternative embodiment of the present invention, the self-retaining braided suture is braided with tissue retainers in two directions (e.g., in approximately opposite directions along the long length of the suture). The sutures with tissue retainers in two directions can be manufactured by introducing tissue retainers in the monofilaments in bidirections (i.e., with tissue retainers in both direction along the length of the filament) or by tissue retainer insertion after the monofilaments are braided. In another embodiment of the present invention, a bidirectional self-retaining braided suture is constructed by braiding the suture with tissue retainers inserted into the yarns (i.e., a collection of self-retaining monofilaments) in one direction and have other self-retaining yarn fed into the braid forming point with the tissue retainer direction in the opposite direction. For example, a typical U.S.P. size 1 braided suture is constructed with 16 sheath yarns, with each yarn being a collection of smaller monofilaments (typically referred to as a "multifilament" yarn). In this example, eight of the multifilament sheath yarns can have the tissue retainers in one direction whereas the other eight multifilament sheath yarns can have the tissue retainers in the opposite direction. This embodiment also includes the use of bidirection self-retaining yarns in the multifilament yarns. This embodiment also include the use of a non-systemic number of multifilament yarn in one direction verses the opposite direction. This embodiment includes the use of a standard (i.e., core with no tissue retainers) or self-retaining suture core.

In an embodiment of the present invention, a bioabsorbable multifilament self-retaining braid is coated with a thin layer of coating material which can allow the braided self-retaining suture to pass through tissue during suturing and also allow the self-retaining suture to grip the tissue once the suture is in place. In various embodiments of the present invention, the self-retaining braided suture coating includes natural wax, synthetic wax, synthetic bioabsorbable polymers (e.g., low viscosity glycolic acid polymers, lactic acid polymers, trimethylene carbonate polymers, paradioxanone polymers, epsilon-caprolactone polymers, polyhydroxyalkanoates, urethane materials, and the like, including combinations of two or more of these bioabsorbable materials), natural bioadsorbable polymers such as collagen and non-bioabsorbable materials such as silicones. Likewise, the coating material can be collagen or urethane where either material can be processed to bioabsorbable relatively rapidly or to bioabsorbable relatively slowly. In the case of gluderaldahyde treated collagen, the time taken for the coating to be bioabsorbed can therefore be relatively long or short.

In an embodiment of the present invention, a wax coating is used where the melting (or softening) temperature is near body temperature (37° C.). In an embodiment of the present invention, the wax is a solid, semi-solid, or super-cooled liquid and coats the tissue retainers as the suture is sewn into the body, but quickly softens or melts allowing the tissue retainers to immediately catch into the desired tissue securing the suture line. In an embodiment of the present invention, the wax can be either natural or synthetic, or a combination of the both. In an embodiment of the present invention, natural and/or synthetic additives can be used to improve the desired properties of the wax coating.

In an embodiment of the present invention, a hybrid 'synthetic/recombinant' monofilament suture is generated with a coaxial construction where the core is a non-bioabsorbable material such as polypropylene or polybutester and with a recombinant expressed bioabsorbable PHA polymer covering the core material, and tissue retainers can be introduced into this hybrid suture. In an embodiment of the present invention, the hybrid coaxial 'synthetic/recombinant' suture can have tissue retainers introduced unidirectionally or bidirectionally. In an alternative embodiment of the present invention, a hybrid 'synthetic/non-recombinant' monofilament suture is generated with a coaxial construction where the core is a non-bioabsorbable material such as polypropylene or polybutester and with a non-recombinant bioabsorbable homo or copolymer consisting of one or more of glycolic acid polymers, l-lactic acid polymers, d-lactic acid polymers, trimethylene carbonate polymers, para-dioxanone polymers, epsilon-caprolactone polymers, covering the core material, and tissue retainers are introduced in this hybrid suture. In an embodiment of the present invention, the hybrid coaxial 'synthetic/non-recombinant' expressed suture can have tissue retainers introduced unidirectionally or bidirectionally. In another embodiment of the present invention, a hybrid 'natural/recombinant' monofilament suture is generated with a coaxial construction where the core is a natural material such as silk or collagen with the bioabsorbable rPHA polymer extruded over the core material, and tissue retainers introduced in this hybrid suture. In an embodiment of the present invention, the hybrid coaxial 'natural/recombinant' suture can have tissue retainers introduced unidirectionally or bidirectionally. In a further embodiment of the present invention, a hybrid 'natural/synthetic' monofilament suture is generated with a coaxial construction where the core is a natural material such as silk or collagen with a synthetic bioabsorbable polymer extruded over the core material, and this hybrid suture can have tissue retainers introduced. In an embodiment of the present invention, the hybrid coaxial 'natural/synthetic' suture can have a silk core and a PDO outer layer. In an embodiment of the present invention, the hybrid coaxial 'natural/synthetic' suture can have tissue retainers introduced unidirectionally or bidirectionally. In various embodiments of the present invention, the configurations of the core to the outer layer can be spherical-coaxial. In alternative embodiments of the present invention, the configurations of the core to the outer layer can be pie shaped-coaxial.

In an embodiment of the present invention, self-retaining monofilament yarns can be generated by using a laser as the tissue retainer cutting device. Nano machining of polymers utilizes a variety of different wavelength lasers to ablate polymers including polymethyl methacrylate (PMMA), polypropylene (PP) and polyethylene (PE) immersed in a variety of media including air, methanol and ethanol. Selection of appropriate pulsing of the laser beam and also a polymer with an appropriate glass transition temperature can be used to adjust the dimensions and characteristics of the tissue retainer formed from the polymer. In an embodiment of the invention, ultra violet and/or visible wavelength lasers (190-800 n.m.) are used to ablate synthetic organic polymers. In an embodiment of the invention Kr-fluoride excimer, Nd:YAG and Ti:Sapphire laser can be used to ablate sutures made at least in part from polymers including PGA, PHA, PMMA, PPG, PS, PP and PE. In an alternative embodiment of the invention, off resonance free electrons can be used to ablate polymer material from a suture either alone or in combination with different wavelength lasers to generate a self-retaining suture. In an embodiment of the invention, immersion of the suture in an organic solvent prior to and/or during laser ablation can be used to control the tissue retainer size and/or depth (100 nanometers-100 micrometers) that the tissue retainer is etched in the suture. Alternatively, shorter wavelength $CO_2$ infra red lasers can be used to etch suture polymer material, albeit sacrificing the precision of position and angle of the tissue retainer on the suture. (Annu. Rep. Prog. Chem., Sect. C: Phys. Chem. (2005) 101: 216-247 entitled "8 Studies on laser ablation of polymers"). In an embodiment of the present invention, a self-retaining bioabsorbable monofilament can be generated by using a laser as the tissue retainer cutting device. In an alternative embodiment of the present invention, a self-retaining nonbioabsorbable monofilament material can be generated by using a laser as the tissue retainer cutting device. In another embodiment of the present invention, a self-retaining hybrid coaxial suture can be generated by using a laser as the tissue retainer cutting device. In various embodiments of the present invention, the monofilament yarns have U.S.P. suture size 7/0 and smaller. In alternative embodiments of the present invention, the monofilament yarns have U.S.P. size 8/0 diameter and/or larger diameters.

In an embodiment of the present invention, the tissue retainer cutting process is improved by cooling the suture material before the tissue retainer insertion process. The reduction in temperature will reduce static charging of inserting tissue retainers in the material which can improve the self-retaining suture formation/manufacturing process. In an embodiment of the present invention, the tissue retainer cutting process is improved by cooling the suture material while inserting the tissue retainers. This can be achieved by processing the suture material in a reduced temperature area (i.e., via refrigeration) or by directing a cooling gas or liquid onto or in the vicinity of the suture. For example, liquid nitrogen can be directed onto the suture. Alternatively, refrigerated air or other gases can be used to chill the suture material prior to inserting the tissue retainers.

In an embodiment of the present invention, the monofilament is drawn while inserting tissue retainers to improve the tissue retainer insertion process. Specifically, the process of 'drawing' a monofilament is to apply tensile loads above the elastic deformation point of the material. The stretching caused by these loads yields a permanent elongation of the original filament length. The drawing results in an optimal orientation of the molecules inside the fiber for alignment of the tissue retainers during the tissue retainer insertion process.

The crystal transitions of Nylon 11 annealed and drawn at different temperatures ($T_d$) with different drawing ratios (n) indicate that the Nylon crystal transitions strongly depend on the thermal history and the conditions of drawing. The δ'-form Nylon 11 can be gradually transformed into the α-form when it is drawn at high temperature. However, the α-form was only partly transformed into the δ'-form when it was drawn at low temperature. This is due to the effect of the competition between thermal inducement and drawing inducement. The thermal inducement favors the α-form, while the drawing inducement favors the δ'-form. In an embodiment of the present invention, different temperatures and different drawing ratios can be utilized to favor formation of appropriate crystal transitions in the suture fibers prior to the tissue retainer insertion process. In an embodiment of the present invention, a monofilament is 'under-drawn', i.e., generated at a reduced drawing ratio but normal or elevated temperature in order to favor the thermal inducement preferred form or generated at a reduced temperature but normal or elevated drawing ratio in order to favor the drawing inducement preferred form. Alternatively, combinations of these processes can be used to further induce a preferred form or in order to reverse the preferred form before the tissue retainer insertion. In an embodiment of the present invention, the monofilament can be extruded at a reduced drawing ratio but normal temperature and then the monofilament can be drawn at an increased ratio during tissue retainer insertion process. In an alternative embodiment of the present invention, the monofilament can be extruded at a normal drawing ratio but decreased temperature and then the monofilament can be drawn at an increased temperature during tissue retainer insertion process. Additional monofilament draw processes and/or relaxation processes can be used to optimize the desired properties of the self-retaining monofilament sutures. A monofilament relaxation step is when the relative tension on the monofilament is reduced, and this relaxation process can be carried out at reduced temperatures, room temperature, or elevated temperatures. In an embodiment of the present invention, the relaxation step(s) can be carried out in a continuous manner (e.g., with the self-retaining suture moving between textile godets which apply the desired tensile load). In an embodiment of the present invention, the relaxation step(s) can be preformed as a batch process. In an embodiment of the present invention, multiple monofilament fibers (i.e., a multifilament yarn) can have tissue retainers introduced at the same time in a similar manner as the above monofilament self-retaining-drawing embodiments. In these embodiments, the temperature or drawing ratio may be adjusted to result in a preferred form of one or more of the constituents of the multifilament yarn. For example, in a coaxial suture, the preferred form from a strength perspective of the inner fiber may be generated during extrusion, while the preferred form of the outer layer from a tissue retainer insertion perspective may be generated prior to tissue retainer insertion.

In an embodiment of the present invention, the suture comprises polymer materials which exhibit complex elastic-plastic deformation profiles. Polybutesters have different block crystalline zones which cold-work at different tensile loads and therefore yield an elastic-plastic deformation profile which can be approximated by two different elastic-plastic deformation profiles superimposed but offset from each other. In an embodiment of the present invention, the suture comprises polybutester filaments. In an embodiment of the present invention, polymer materials which exhibit complex elastic-plastic deformation profiles allow for tissue retainer insertion of materials which exhibit high strength plastic deformation while retaining a relatively good elastic profile well above a typical polymer plastic deformation point. These properties can be especially useful for self-retaining insertion suture materials used for cardiac self-retaining sutures.

Figure 2:
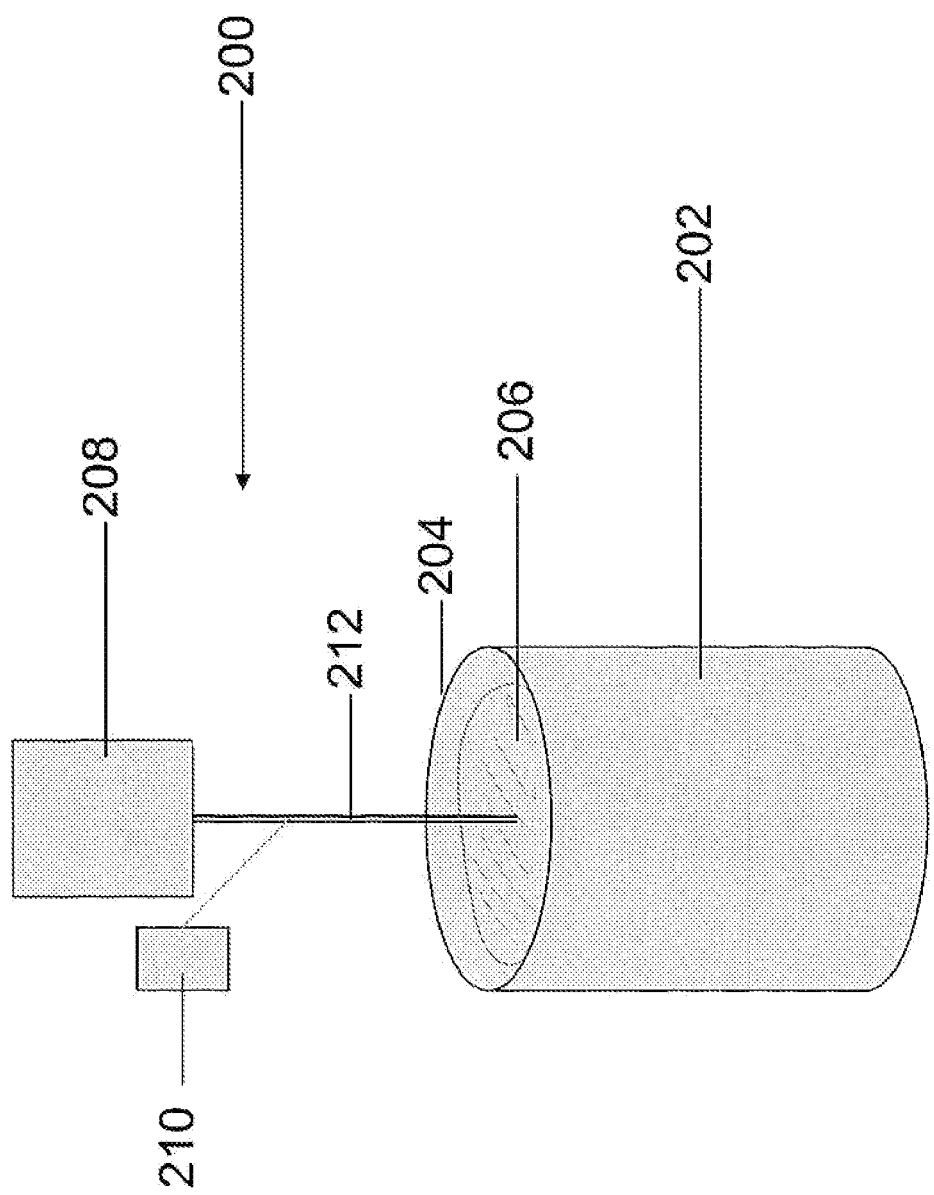
FIG. 2 is a perspective view of another embodiment of a tissue retainer forming device of the present invention.

In an embodiment of the present invention, a testing procedure to determine the strength of a self-retaining suture uses a potting material to retain one end of a self-retaining suture to yield a consistent test. In an embodiment of the present invention, a self-retaining suture can be inserted in a container and the container can be partially filled with a liquid or gel which cures into a solid, then the potted end of the self-retaining suture can be secured and the free end of the self-retaining suture can be tensile pulled using a standard tensile testing machine. The container may take any three-dimensional configuration, including a vertical cylinder, a cube, a cone, a sphere, and so forth. In an embodiment of the present invention, a self-retaining suture can be inserted in a vertical cylinder and the cylinder can be partially filled with a silicone potting compound (for example, room temperature curing silicone) for tensile testing. In various alternative embodiments of the present invention, a hydrogel can be used as the potting compound. In an embodiment of the present invention, CoSeal™ can be used as the potting compound to secure the self-retaining suture to yield a consistent test. In an alternative embodiment of the present invention, Confluent Surgical DuraSeal™ can be used as the potting compound. In an embodiment of the present invention, a self-retaining suture can be inserted in a vertical cylinder and the cylinder can be partially filled with collagen for tensile testing. In various embodiments of the present invention, the collagen can be non-solvated or solvated. In another embodiment of the present invention, animal fat (such as pig fat or cattle fat) can be used as the potting material for the self-retaining suture test. In an alternative embodiment of the present invention, synthetic wax can be used as the potting compound. In various embodiment of the present invention, the potting compound can be non-crosslinked, semi-crosslinked or crosslinked to improve the holding strength of the potting compound with respect to the self-retaining suture. In alternative embodiments of the present invention, the temperature of the potting compound can be adjusted to improve the holding strength of the potting compound with respect to the self-retaining suture. In various embodiment of the present invention, other potting materials can be selected from the set consisting of "foam-in-place" materials, ultraviolet light cross-link sensitive polymers, clays, rubber, packed powder and cement. In an embodiment of the present invention, a testing apparatus is provided for carrying out various methods of the invention. As shown in FIG. 1, testing apparatus 100 includes a container 102, container 102 having at least one open end 104 and potting material 106, and a tensile testing machine 108. To carry out various testing methods of the present invention, one end of a suture 110 may be inserted into potting material 106 while the other end of suture 110 may be attached to tensile testing machine 108. The testing apparatus may be adapted to provide a suture retainer forming apparatus, according to an embodiment of the invention. For example, as shown in FIG. 2, suture retainer forming apparatus 200 includes a container 202, container 202 having at least one open end 204 and potting material 206, a tensile testing machine 108, and a tissue retainer cutter 210. When one end of a suture 212 is in the potting material 206 and the other end of the suture 212 is attached to tensile testing machine 208, cutter 210 may be used to form tissue retainers on suture 212. In various embodiments of the suture retainer forming apparatus of the invention, the cutter may be, without limitation, a laser, a blade, a grinding wheel, or a cutting disc.

In an embodiment of the present invention, self-retaining sutures can be generated from twisted collagen filaments which have been chemically crosslinked to improve the cat-gut suture strength and increase the bioabsorption time. In an embodiment of the present invention, self-retaining sutures can be generated from catgut sutures which have been treated with gluderaldahyde. Catgut sutures are traditional low-strength and relatively fast absorbing sutures made from twisted collagen. Because of the twisted ribbon-like nature of catgut suture (such as plain and chromic acid treated catgut sutures), these filaments are generally not suitable as self-retaining sutures. However, by treating the collagen with cross-linking reagents such as gluderaldahyde, an extremely durable and long lasting collagen suture can be made with monofilament-like properties. Common catgut suture manufacturing methods including treating with hydrogen peroxide, bleaching agents, chromic acid, oxidizing reagents, acids, twisting, drying, and center less grinding can be performed prior to crosslinking. In an embodiment of the present invention, the chemical crosslinking can be carried out before the tissue retainers are cut into the collagen suture. In an embodiment of the present invention, the chemical crosslinking can be carried out after the tissue retainers are cut into the collagen suture. A gluderaldahyde treaded catgut suture can have tissue retainers introduced into a low cost self-retaining suture which can be manufactured to be essentially non-bioabsorbable. Any source of collagen can be used to make collagen fibers which in turn can be used to make collagen sutures.

In an alternative embodiment of the present invention, prior to tissue retainer insertion a collagen suture is coated with a compound comprising one or more of an absorbable collagen coating, a non-absorbable collagen coating, an absorbable urethane coating, a synthetic bioabsorbable polymer coating, a non-absorbable polymer coating.

Approximately with respect to temperature means ±10% of the stated temperature, i.e., approximately 50° C. includes the range 45-55° C. Approximately with respect to extension to break strength means ±10%, i.e., approximately 40% extension to break strength includes the range 38%-46% extension to break strength.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. A device for testing extension-to-break strength of a suture comprising:
   a container, wherein the container has at least one opening, wherein the container is adapted such that a first end of the suture can be inserted into an opening in the container such that the first end is inside the container;
   potting material, wherein the potting material is inserted into the container and molds to the shape of the first end of the suture and the inside of the container, wherein the potting material can be chemically or physically transformed to retain the first end of the suture in the container; and
      a tensile testing machine, wherein a second end of the suture is attached to the tensile testing machine.

2. The device of claim 1, wherein the potting material is selected from the group consisting of a silicone gel, a hydrogel, collagen, synthetic wax, 'foam-in-place' material, ultraviolet light cross-link sensitive polymers, clays, rubber, packed powder and cement.

3. The device of claim 1, wherein addition of a further reagent to the potting material activates a chemical reaction which solidifies the potting material.

4. The device of claim 1, wherein irradiation of the potting material with one or more wavelengths of light activates a chemical or physical reaction which solidifies the potting material.

5. A method of testing a self-retaining suture comprising:
   inserting a first end of the suture in a container, wherein the container is hollow at a first end and sealed at a second end;
   filling the container with potting material, allowing the potting material to mold to the shape of the first end of the self-retaining suture in the container,
   chemically or physically transforming the potting material to retain the first end of the self-retaining suture in the container; and
   attaching a second end of the self-retaining suture to a tensile testing machine, wherein the tensile testing machine draws and monitors the integrity of the self-retaining suture with increasing tensile strength applied.

6. The method of claim 5, wherein the potting material is selected from the group consisting of a silicone, a hydrogel, collagen, synthetic wax, "foam-in-place" materials, ultraviolet light cross-link sensitive polymers, clays, rubber, packed powder and cement.

7. The method of claim 5, further comprising addition of a further reagent activates a chemical or physical reaction in the potting material, wherein the chemically or physically reacted potting material retains the self-retaining suture in the container.

8. The method of claim 5, further comprising irradiation of the potting material with one or more wavelengths of light activates a chemical or physical reaction in the potting material, wherein the chemically or physically reacted potting material retains the self-retaining suture in the container.

9. A device for cutting a tissue retainer in a small monofilament suture comprising:
   a container, wherein the container has an opening, wherein the container is adapted such that a first end of the monofilament suture can be inserted through the opening into the container;
   potting material, wherein the potting material is inserted into the container and molds to the shape of the first end of the monofilament suture in the container, wherein the potting material is chemically or physically transformed to retain the first end of the monofilament suture in the container;
   a tensile machine, wherein a second end of the monofilament suture is attached to the tensile machine; and
   a cutter, wherein the cutter is directed onto the monofilament suture to cut the tissue retainer.

10. The device of claim 9, wherein the cutter is a laser.

11. The device of claim 9, wherein the potting material is selected from the group consisting of a silicone, a hydrogel, collagen, synthetic wax, "foam-in-place" materials, ultraviolet light cross-link sensitive polymers, clays, rubber, packed powder and cement.

12. The device of claim 9, wherein addition of a further reagent activates a chemical reaction which solidifies the potting material to retain the first end of the monofilament suture in the container.

13. The device of claim 9, wherein irradiation of the potting material with one or more wavelengths of light solidifies the potting material to retain the first end of the monofilament suture in the container.

14. The device of claim 9, further comprising a chamber or substrate in which the temperature can be increased or decreased in order to increase or decrease the temperature of the suture prior to cutting the tissue retainer.

15. A method of cutting a tissue retainer in a small monofilament suture comprising:
   inserting a first end of the monofilament suture in a container;
   filling the container with potting material;
   allowing the potting material to mold to the shape of the first end of the monofilament suture in the container;
   chemically or physically transforming the potting material to retain the first end of the monofilament suture in the container;
   attaching a second end of the monofilament suture to a tensile testing machine, wherein the tensile testing machine draws and monitors the integrity of the suture with increasing tensile strength applied; and
   directing a cutter onto the monofilament suture to cut the tissue retainer.

16. The method of claim 15, further comprising drawing the monofilament suture prior to cutting the tissue retainer.

17. The method of claim 15, further comprising one or both heating and cooling the monofilament suture prior to cutting the tissue retainer.

18. The method of claim 15, further comprising changing one or both the tensile drawing force and the temperature of the monofilament suture prior to cutting the tissue retainer.

19. The method of claim 18, further comprising a relaxation step prior to changing one or both the tensile drawing force and the temperature of the monofilament suture prior to cutting the tissue retainer.

20. The method of claim 15, wherein the cutter is a laser.

* * * * *